United States Patent [19]

Roffman

[11] Patent Number: 5,050,981
[45] Date of Patent: Sep. 24, 1991

[54] LENS DESIGN METHOD AND RESULTING ASPHERIC LENS

[75] Inventor: Jeffrey H. Roffman, Jacksonville, Fla.

[73] Assignee: Johnson & Johnson Vision Products, Inc., Jacksonville, Fla.

[21] Appl. No.: 557,261

[22] Filed: Jul. 24, 1990

[51] Int. Cl.⁵ .......................... G02C 7/02; G02C 7/04
[52] U.S. Cl. ................................. 351/177; 351/159; 351/161; 351/167
[58] Field of Search ............... 351/160 R, 160 H, 161, 351/162, 159, 167, 177

[56] References Cited

U.S. PATENT DOCUMENTS 3,482,906 12/1969 Volk .................................. 351/160 R
4,564,484 1/1986 Neefe .................................. 264/2.6
4,640,595 2/1987 Volk .................................. 351/160 R
4,710,193 12/1987 Volk .................................. 623/6

Primary Examiner—Scott J. Sugarman
Attorney, Agent, or Firm—Joel R. Petrow

[57] ABSTRACT

An aspheric lens for providing improved vision and a method for generating such a lens is described. The lens provides a sharp image focus while minimizing image aberrations. The method utilizes ray tracing techniques in conjunction with Modulation Transfer functions to accurately account for the total corrective lens-eye system. The lens may be in the form of a contact lens, an intraocular lens, a natural lens or a spectacle lens, and is suitable for correcting myopia, presbyopia, astigmatism and other focusing problems. The lens is characterized by a hyperbolic or parabolic surface which functions to reduce spherical aberrations and minimize the retinal image spot size.

6 Claims, 9 Drawing Sheets

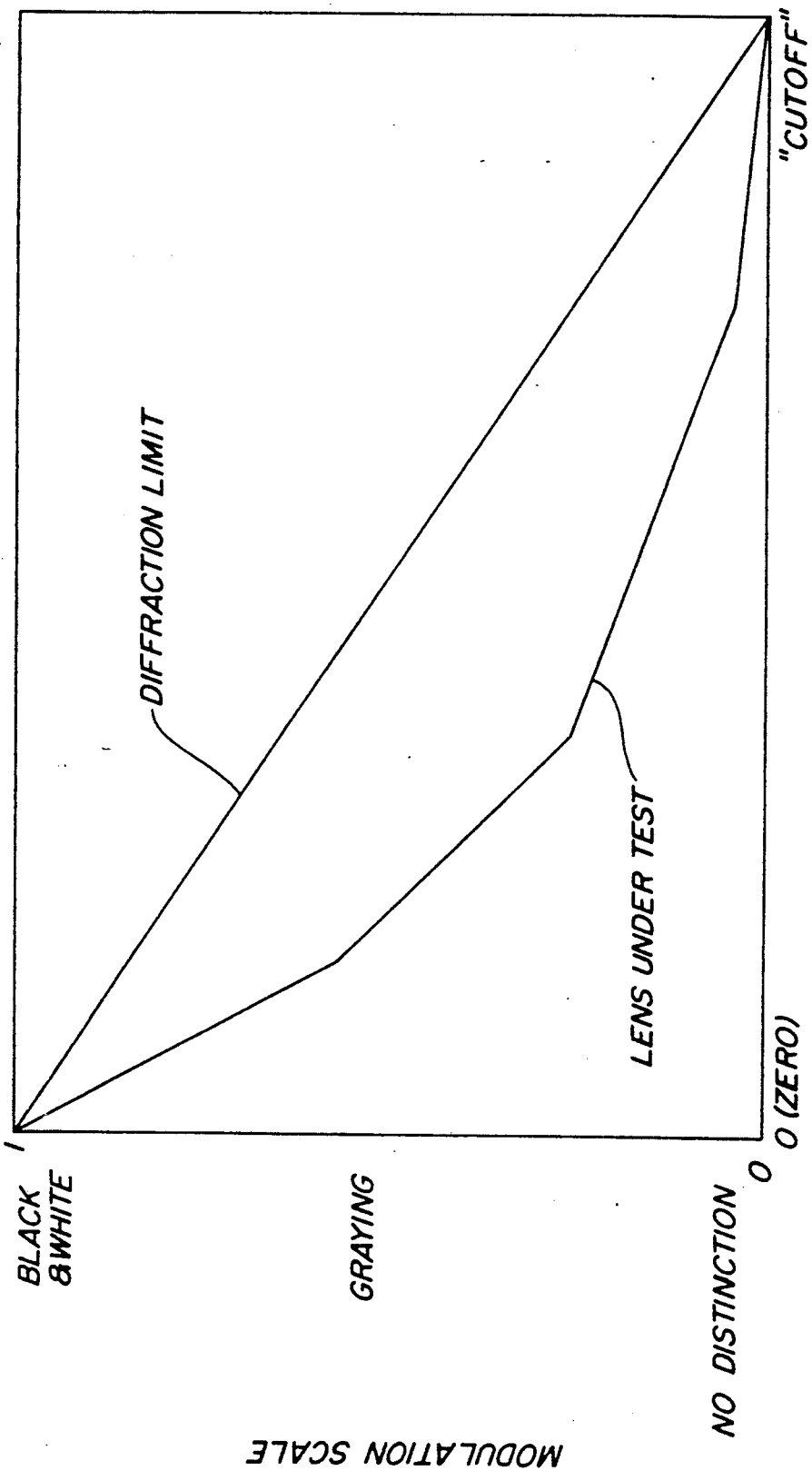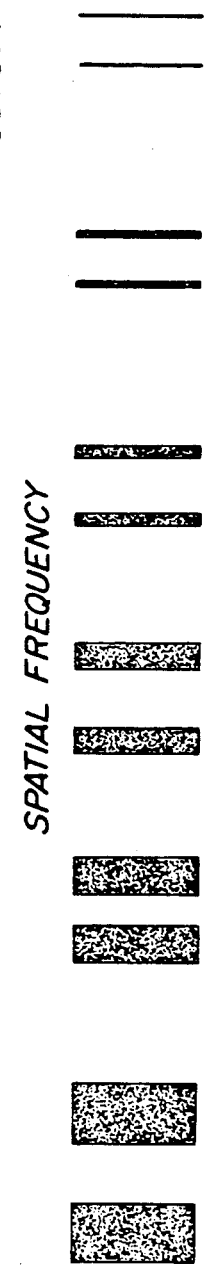

LENS DESIGN METHOD AND RESULTING ASPHERIC LENS

BACKGROUND OF THE INVENTION

This invention is a method for designing a lens to provide an optimal corrective lens-eye system having minimal image aberrations and the resulting lens having an aspheric surface for use as an contact, intraocular or spectacle lens, particularly a lens in which the surface has a hyperbolic or parabolic curvature.

The curvature of a conventional lens surface may be described in terms of "conic sections." The family of conic sections includes the sphere, parabola, ellipse, and hyperbola. All rotationally symmetric conic sections may be expressed in terms of a single equation:

$$X = \frac{Y^2}{r + [r^2 - (\kappa + 1)Y^2]^{\frac{1}{2}}}$$

where X is the aspheric surface point at position Y, r is the central radius, and the kappa factor, $\kappa$, is the aspheric coefficient.

Other conic constants or aspheric coefficients include the eccentricity, e, which relates to $\kappa$ by the equation $\kappa = -e^2$, and the rho factor, $\rho$, defined as $(1-e^2)$.

The value of the aspheric coefficient determines the form of the conic section. For a sphere, e=0 and x=0. An ellipse has an eccentricity between 0 and 1 and a $\kappa$ between 0 and $-1$. A parabola is characterized by an e=1 ($\kappa = -1$). For a hyperbola, e is greater than 1 and $\kappa$ is less than negative one.

Conventionally, most lens surfaces are spherical or near-spherical in curvature. Theoretically, for an infinitely thin lens, a spherical curvature is ideal to sharply focus the light passing through the lens. However, the curvatures and thicknesses of a real lens produce well-known optical aberrations, including spherical aberration, coma, distortion, and astigmatism; i.e., light from a point source passing through different areas of the lens that does not focus at a single point. This causes a certain amount of blurring. Furthermore, purely spherical lenses are not suitable for correcting astigmatic vision or for overcoming presbyopia.

For this reason, many different types of lenses have been designed for the purpose of minimizing spherical aberration, correcting ocular astigmatism, or providing a bifocal effect that allows the nonaccommodative eye to see objects both near and far. Unfortunately, current designs suffer from serious drawbacks, such as producing blurred or hazy images, or inability to provide sharp focusing at every visual distance.

Aspheric lenses having elliptical surfaces have been used to reduce optical aberrations. Some well known examples are the use of parabolic objective mirrors in astronomical telescopes and the use of ellipses of low eccentricity to correct for aberrations of a contact lens.

The design of an aspheric lens in isolation is well known. There are a variety of commercially available software packages that use variations of the above equation to generate aspheric lens designs. An example of these are: Super OSLO by Sinclair Optics, Inc., Code-V by Optical Research Associates and GENII-PC by Genesee Optics, Inc. These optical design programs are the most widely used packages available. Despite the different approaches used by the three methods, all packages have yielded identical results in aspheric lens design calculations. When used alone for vision correction, carefully designed elliptical lenses do provide an improved focus. However, when used in a system including the human eye, elliptical lenses are not significantly better than spherical lenses. This is because the eye contains a greater amount of aberration than the elliptical lens is able to correct as part of the overall corrective lens-eye system.

Methods used in the past to produce corrective lenses for the eye have resulted in lenses that are non-spherical. In U.S. Pat. No. 4,170,193 to Volk a lens is described which corrects for accommodative insufficiency by increasing dioptric power peripheralward. While this lens and other prior lens designs are not strictly spherical, it is not a pure asphere, and includes higher order deformation coefficients. This yields a surface which is radically different than that proposed herein. A flattening curve, such a hyperbola, would show a slight dioptric decrease peripheralward. Prior lens designs, while attempting to solve various optical problems by varying from a strictly spherical lens design, do not strive for improved vision by reducing the aberration of the image that strikes the retina of the eye.

An important reason for the common use of lens designs that have the above-noted limitations is the failure to take into account the effects of the entire lens-eye system. Lenses are usually designed as if the lens would be the only element that contributes to image aberrations, but there are may elements in the eye that affect image focus, such as the surfaces of the cornea and of the eye's natural lens. While the elliptical form was useful in reducing aberrations of the lens itself, when the lens is placed into a system containing all of the refracting surfaces of the human eye additional aspherical correction is required.

SUMMARY OF THE INVENTION

The present invention is that this required correction has been found to be in the form of certain hyperbola or a parabola and provides a lens for effectively focusing light on the retina of the eye and a method for producing such lens. The lens has a rotationally symmetric aspheric surface in the form of a hyperbola or parabola defined by the equation:

$$X = \frac{Y^2}{r + [r^2 - (\kappa + 1)Y^2]^{\frac{1}{2}}}$$

where X is the aspheric surface point at position Y, r is the central radius, and x is a commonly used aspheric constant, wherein the value of x is less than or equal to $-1$.

It is an object of the present invention to provide a method for the systematic approach to the design of an aspheric lens in which the lens is considered and optimized as part of the entire corrective lens-eye system.

It is a further object of the present invention to use the modulation transfer function (the modulation scale from black and white to gray) and the spatial frequency (showing the degree to which objects of increasing spatial frequency can be resolved) to optimize a corrective lens design when considered with the corrective lens-eye system.

An additional object of the present invention is to provide a method that produces a lens that optimizes the focusing of an image on the retina of the eye and that minimizes image aberrations and blurring.

It is an object of the present invention to provide a novel aspheric lens design suitable for use in a contact lens, an intraocular lens, or a spectacle lens.

It is also an object of the present invention to provide a lens for use on the surface of, in or near the human eye wherein a lens surface is curved in the shape of a hyperbola.

It is a further object of the present invention to provide a lens for use on the surface of, in or near the human eye wherein a lens surface is curved in the shape of a parabola.

Another object of this invention is to provide an aspheric lens suitable for use by those suffering from presbyopia, myopia, hyperopia, astigmatism, or other vision focusing deficiencies.

BRIEF DESCRIPTION OF THE DRAWINGS

FIG. 8 is a typical Modulation Transfer Function graph showing the resolving power of the eye with a conventional corrective lens and the inherent limit of resolving power due to diffraction limits.

DETAILED DESCRIPTION OF THE PREFERRED EMBODIMENTS

The present invention applies optical ray trace techniques to an optical schematic of the human eye to achieve heretofore unobtained performance from a corrective lcn-eye system. The human eye model was developed after an extensive literature search on the subject of human ocular physiology, physiological optics and anatomy. In particular, a starting point for the model were the Gullstrand (1862-1930) Schematic Eyes. Gullstrand created these models on the basis of available data on the anatomy of the eye generated by himself as well as other researchers. The Gullstrand eyes contain centered, spherical surfaces, and were used throughout the 20th century to evaluate first order (i.e., location, not level of aberration) image formation of the human eye.

It is recognized that there are individual variations from the averages which Gullstrand presented, and in addition, advances in metrology allowed analysis in greater detail of the refractive index distribution, as well as variations in aspheric curvature of the various elements. Using the Gullstrand Schematic as a starting point, with the addition of more modern knowledge about the anatomy of the eye, a composite eye model was generated.

To first order, the model can be looked at as a three lens compound system, the lenses being the corrective lens devices, the cornea, and the crystalline lens of the eye. This can be further broken down to contain 13 surfaces for the purpose of ray trace analysis. These surfaces are:

1] Object
2] Front surface of the corrective lens
3] Back surface of the corrective lens
4] Tear layer
5] Corneal epithelium
6] Corneal endothelium aqueous interface
7] Pupil in aqueous
8] Lens anterior cortex
9] Lens anterior core
10] Lens posterior core
11] Lens posterior cortex
12] Vitreous
13] Retina It is not usual that the image falls on the retina. Indeed, this is the definition of refractive error. Using ray trace techniques, the actual position relative to the retina and quality of the image can be determined.

Figure 1:
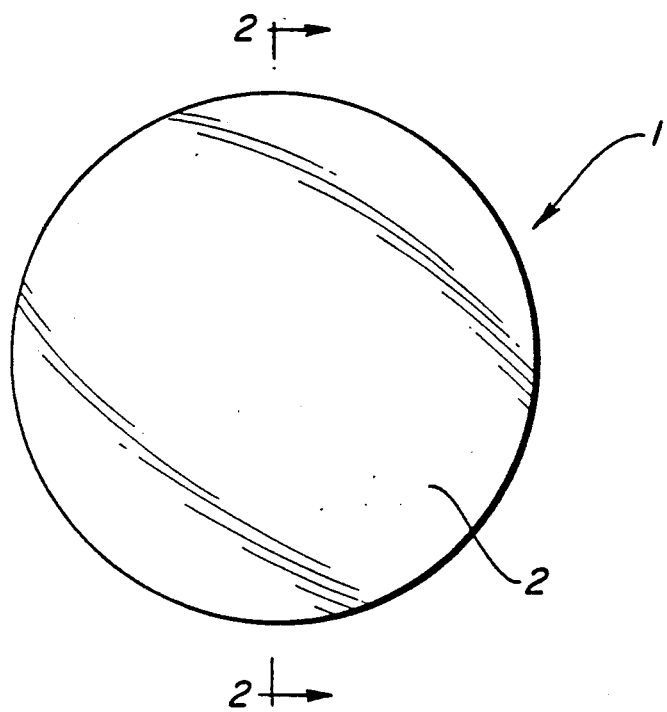
FIG. 1 is a front elevation of a contact lens according to the present invention.
Figure 2:
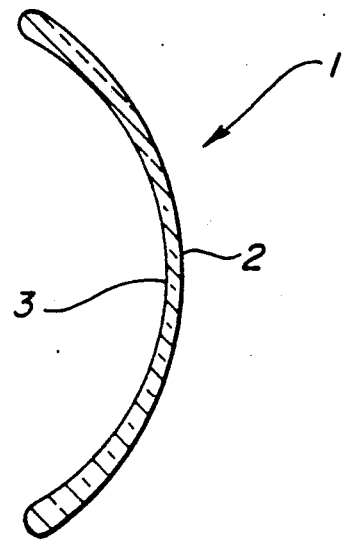
FIG. 2 is a cross sectional view of the lens shown in FIG. 1 taken along the line 2—2.

FIGS. 1 and 2 illustrate one embodiment of a lens 1 according to this invention which is suitable for use as a contact lens. This lens 1 has a rotationally symmetric hyperbolic surface 2 and a concave spherical surface 3. The spherical surface 3 has a radius of curvature which conforms to that of the outer surface of the human eye so that the lens 1 may rest comfortably on the eye surface. The size of the contact lens 1 should be suitable for the intended use, e.g., about 12-15 mm in diameter and no more than about 0.050-0.400 mm thick.

Figure 3:
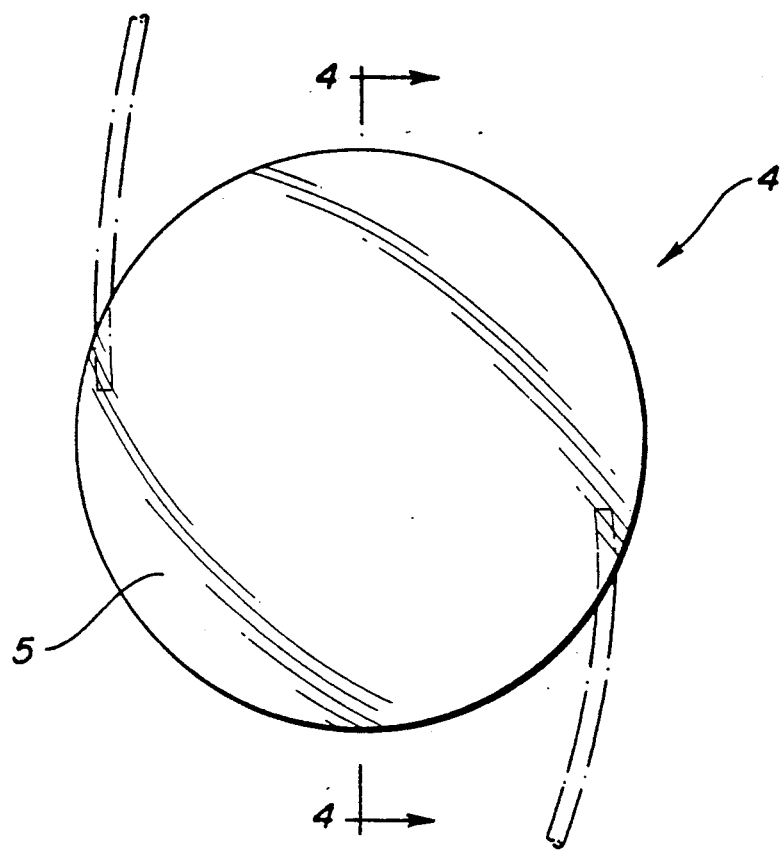
FIG. 3 is a front elevation of an intraocular lens according to the present invention.
Figure 4:
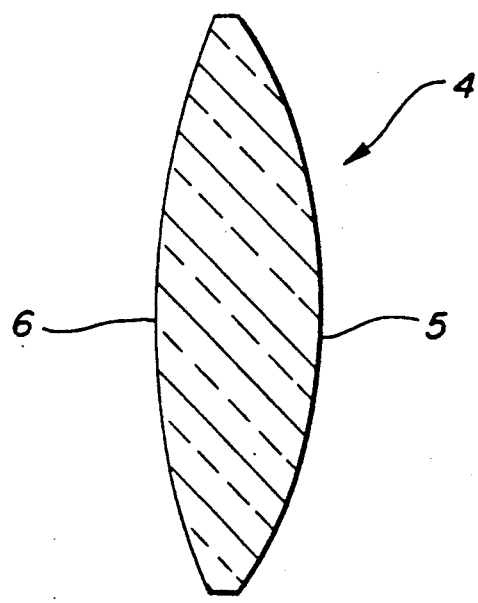
FIG. 4 is a cross section view of the lens shown in FIG. 3 taken along the line 4—4.

FIGS. 3 and 4 illustrate an intraocular lens 4 according to this invention. This lens 4 has a rotationally symmetric hyperbolic surface 5 and a convex spherical surface 6. The intraocular lens 4 should be approximately 4-7 mm in diameter and have a maximum thickness of about 0.7-1.0 mm.

The lenses of this invention are not limited to the physical dimensions given above; these dimensions are only rough guidelines. A lens may be whatever size is suitable for the intended use.

A lens according to this invention may have two symmetric aspheric surfaces rather than one, but at least one surface must be a symmetric asphere as defined by the following equation:

$$X = \frac{Y^2}{r + [r^2 - (\kappa + 1)Y^2]^{\frac{1}{2}}}$$

where X is the aspheric surface point at position Y, r is the central radius, and the kappa factor, $\kappa$, is a commonly used aspheric constant, wherein the value of $\kappa$ is less than or equal to $-1$. Preferably, the curvature is hyperbolic, i.e., $\kappa$ is less than negative one, although a parabolic curvature ($\kappa=-1$) is also within the scope of the invention. The aspheric surface may be convex or concave; where there are two aspheric surfaces, each may independently be convex or concave.

The lens of the present invention minimizes the optical aberrations of the lens/eye system. This produces a sharper focus on the retina, as illustrated in FIG. 5.

Figure 5:
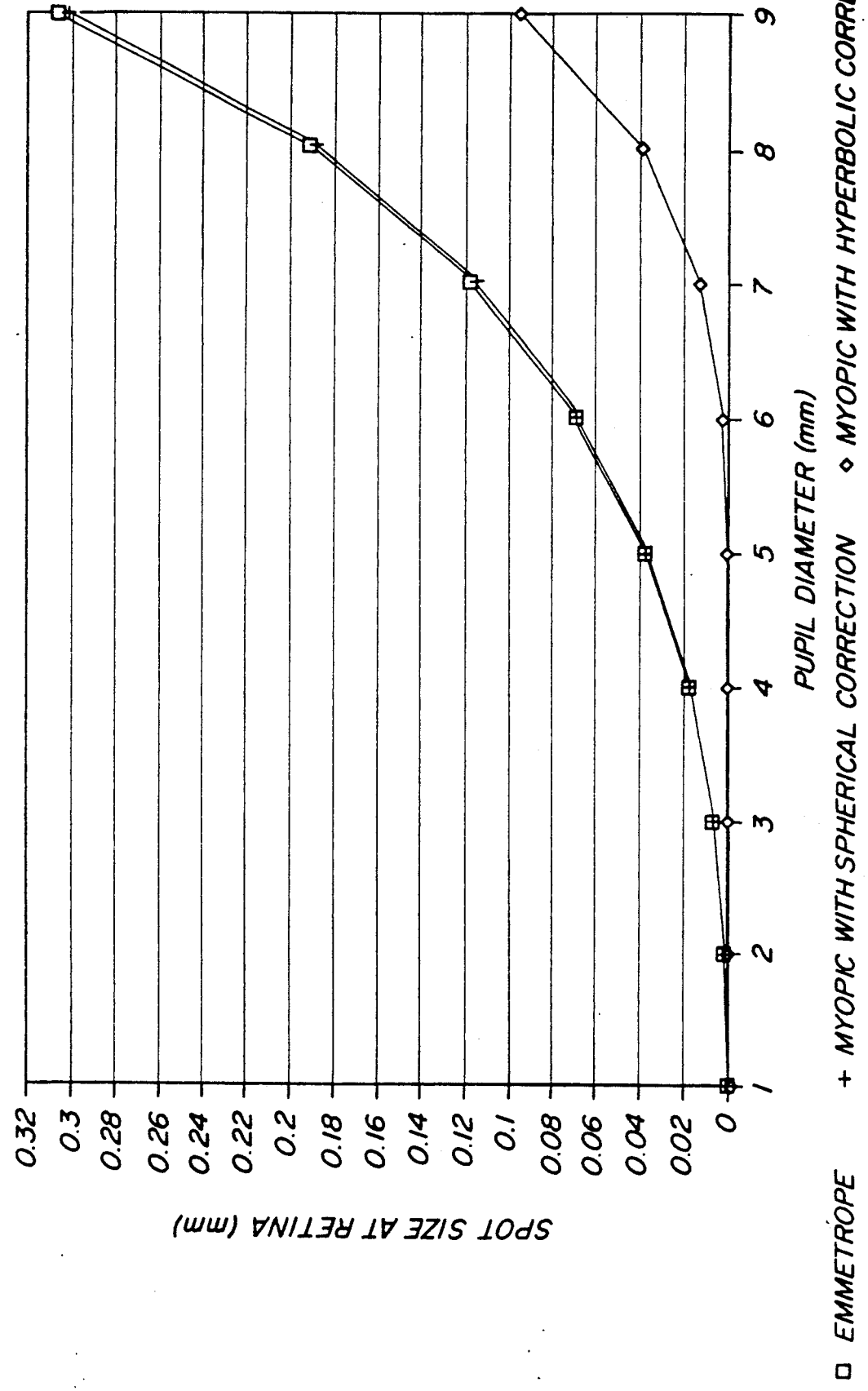
FIG. 5 graphically compares the size of the retinal image of a point light source as a function of pupil diameter for a myopic eye/hyperbolic contact lens system to that of a myopic eye/spherical contact lens system and an emmetropic eye, where each lens has the optimum optical power to correct the myopia of the eye.

FIG. 5 was generated by computer ray tracing methods, and shows that the blur spot size at the retina is much smaller for a myopic eye corrected with a hyperbolic front curve than for either an emmetropic (i.e., normal) eye or a myopic eye corrected by a spherical lens.

Figure 6:
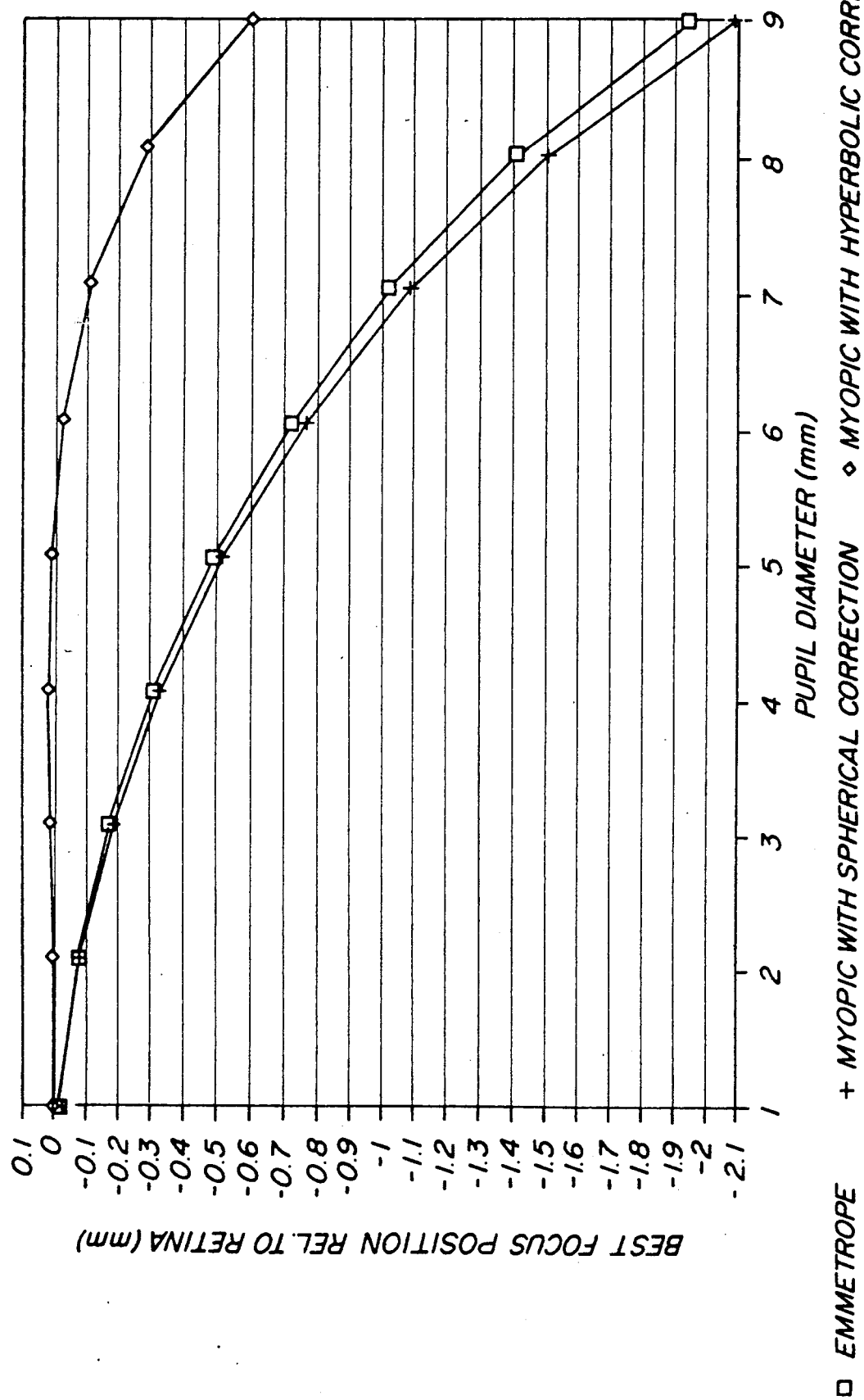
FIG. 6 shows the best focus position relative to the retina for the images of FIG. 5.

Furthermore, the light tends to be more accurately focused on the retina, as shown in FIG. 6. FIG. 6 was generated by a computer ray trace simultaneously with FIG. 5 and shows the position of the focused image is closest to the retina for the hyperbolic lens/eye system.

As a direct result of these advantages, a lens according to the present invention can provide acceptable vision for those who suffer from astigmatism or presbyopia. The usual approach to correcting astigmatism is to provide a corrective lens that is radially asymmetric in complimentary compensation for the radial asymmetry in either the natural eye lens or in the retina. This approach requires the production and inventory of a large number of lenses to suit not only the basic perscription, but also to provide the complimentary radial asymmetry of the eye. Further, the lens must have a means for maintaining its radial position with respect to the eye in order that the radial variation of the lens matches the eye's radial requirements. Means developed heretofore have not performed with total satisfaction.

Compensation for the non-accommodating natural eye lens is traditionally provided by having a divided lens, with two or more focal lengths to provide far and near vision or, as in some recent designs, a diffractive or refractive lens with two or more focal lengths that can provide adequate near and far vision. This type of system, however, divides the incoming light among the various foci and presents each focus at every point on the retina. Obviously this results in a reduction in the amount of light available for any individual focus and in competing images at each point on the retina.

The aspheric lens does not provide visual compensation to the astigmat or presbyop by graded power or multiple focal lengths, but improves the corrective lens/eye system to the point where, despite the variations caused by asigmatism or presbyopia, the overall performance falls within or near the range of visual acuity of the normal individual.

This occurs because the aforementioned spot size of each point falling on the retina is reduced below that possible by the unaided emmetropic eye alone which contains a natural spherical lens. Because of the optical superiority of the aspheric corrective lens/eye system, the blur of a point on the retina introduced by presbyopia or astigmatism is offset by the aspheric improvement and is thereby less than (or in the range of) that found in the normal eye.

With the proper prescription, virtually any focusing deficiency may be corrected by this lens Typically, a lens according to the present invention will have an optical power between about +20.00 and about −20.00 diopters.

Figure 7:
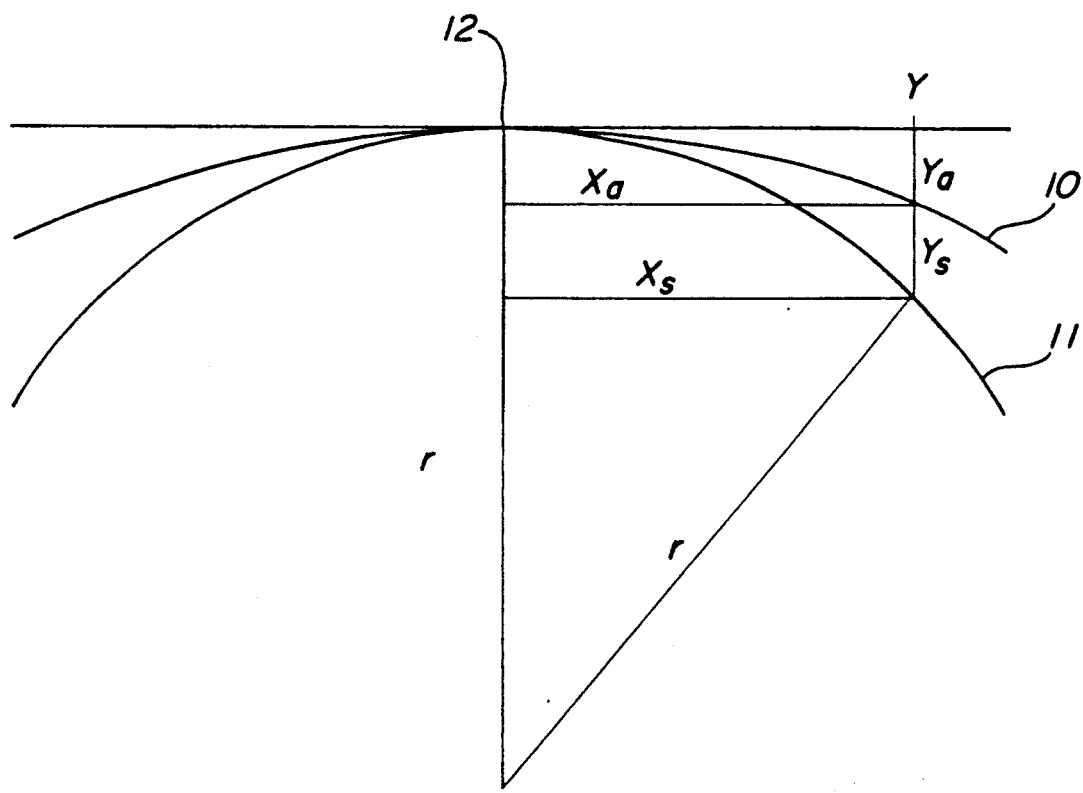
FIG. 7 graphically compares the curvature of a spherical surface and an aspheric surface having the same central or apical radius.
Figure 9A:
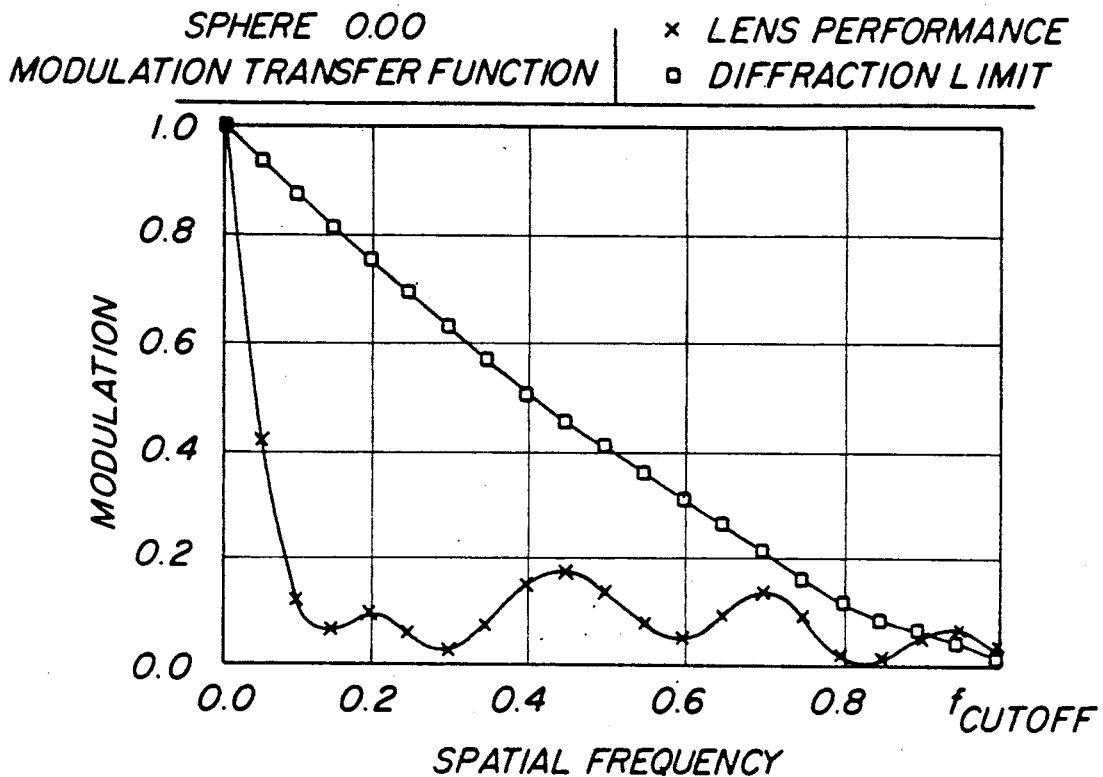
FIG. 9A through F compare the modulation transfer frequency to the diffraction limit in a lens-myope system. Each figure presents the comparison for a particular kappa factor, ranging from $\kappa=0$ in FIG. 9A to $\kappa=-2.5$ in FIG. 9F.
Figure 9B:
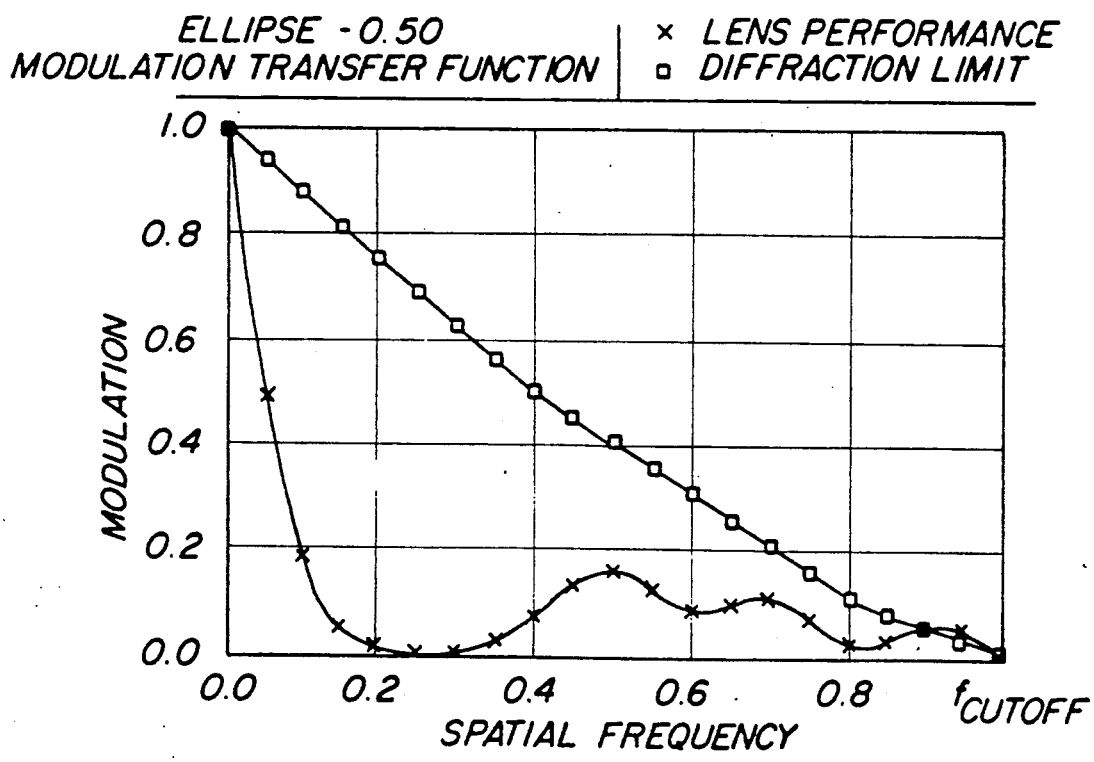
Figure 9C:
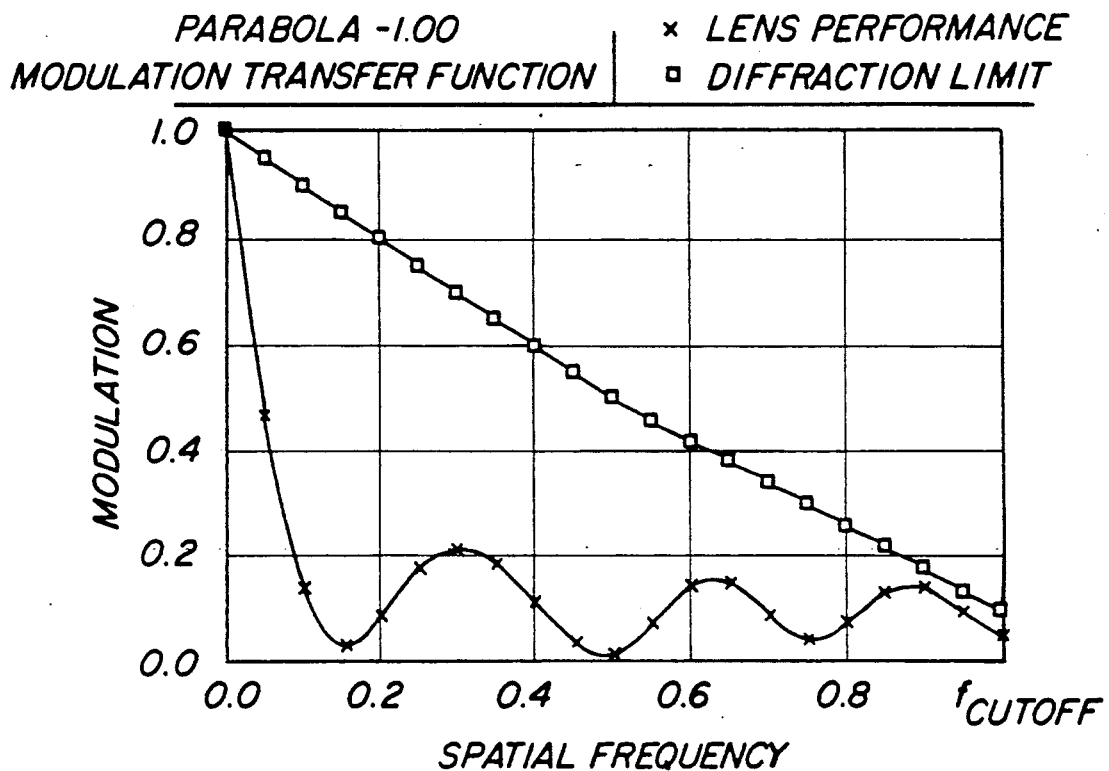
Figure 9D:
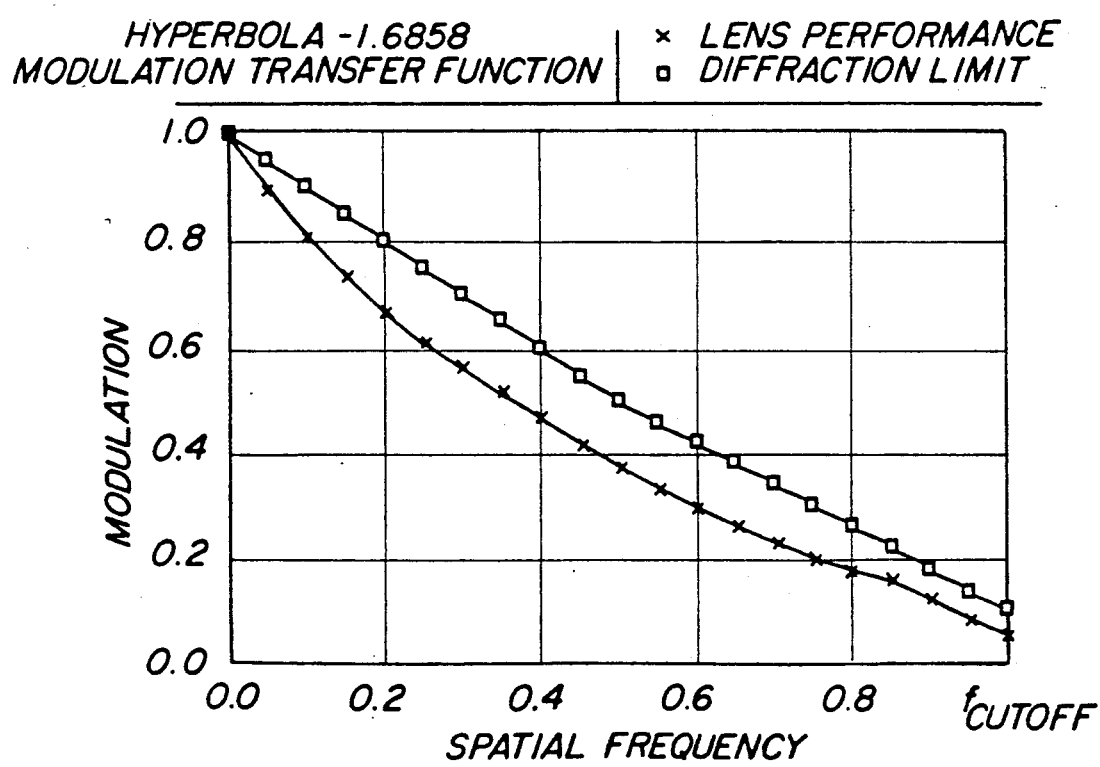
Figure 9E:
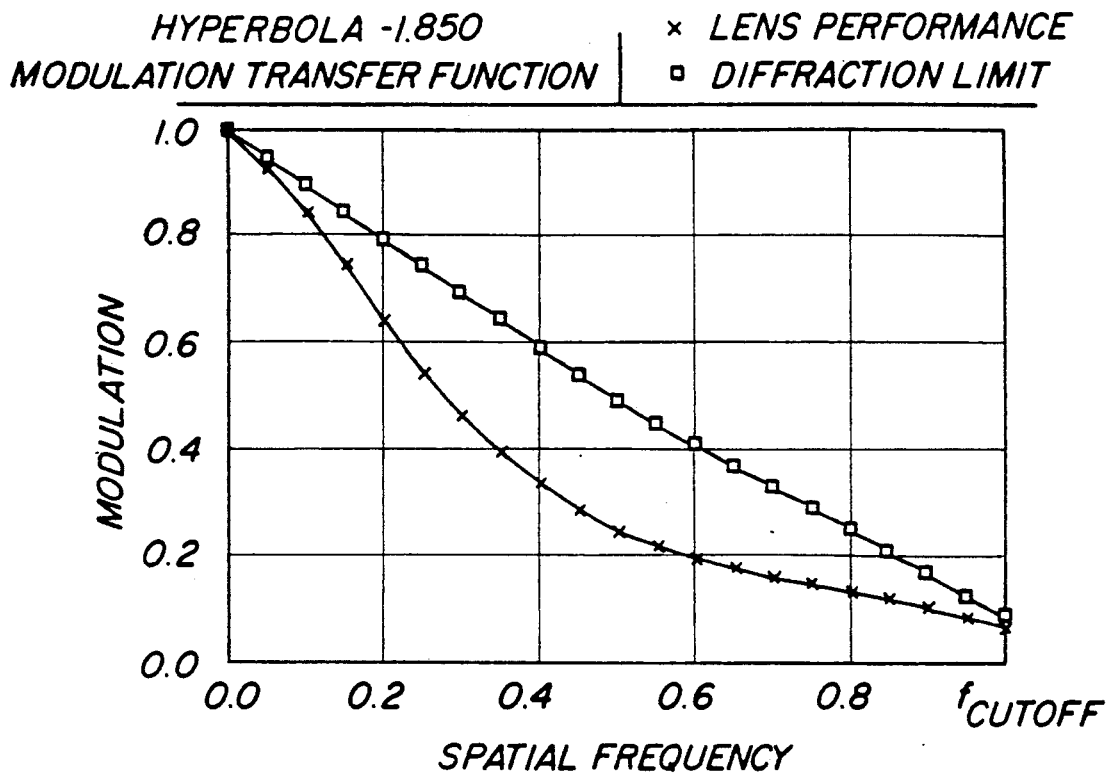
Figure 9F:
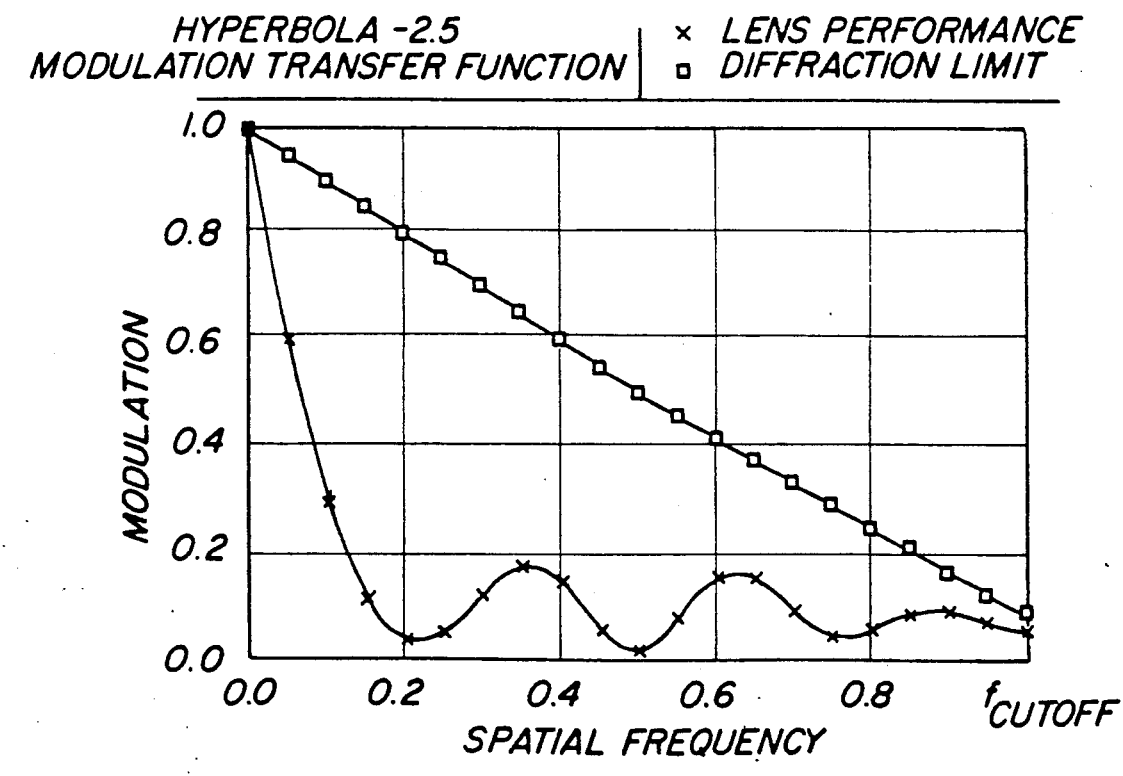

FIG. 7 illustrates the difference between an aspheric curve 10 as defined in the above equation and a spherical curve 11, where both curves have the same apical radius, r. For a given distance from apex 12, $x_a$ or $X_s$, there is a point $Y_a$ on the aspheric curve 10 and a point $y_s$ on the spherical curve 11. The further $X_a$ or $X_s$ is from the apex 12, the greater the difference $y_s - Y_a$.

A lens having the aforesaid properties is designed by a method wherein ray tracing techniques are used to calculate the path of light rays through a corrective lens/eye system, using a sophisticated mathematical model of a human eye and a corrective lens. The thickness, curvature, and material-dependent refractive index of the lens is varied mathematically and ray tracing calculations are performed on each variation to find the optimal lens for a given eye. The optimal lens is one which results in a sharp focus and a minimum of image aberrations. It has been found that in most cases the optimal lens will have a kappa factor in the range of about −1 to about −2.

Image analysis involves the tracing of a large number of rays through an optical system. The fundamental equation for tracing a ray, i.e., determining the angle of the ray and its position) from one optical medium to another, via an interface between the media, is by the classic and fundamental Snell's Law equation: $n_1 \sin \theta_1 = n_2 \sin \theta_2$. For a system of 13 surfaces, this can be very time consuming for even a single ray. Multiple ray analysis using several hundred rays takes a considerable number of operations for even a simple single element lens.

Images can be analyzed in a number of different ways. The classical Seidel aberrations, or reductions in image quality can be calculated by tracing only a few rays. A widely accepted method of quantifying image quality is the MTF, or Modulation Transfer Function. This can be thought of as an extension of previous limiting resolution methods.

Referring to FIG. 8, MTF provides modulation, or contrast, resolution (measured from zero to one) versus spatial frequency or fine detail size of an object. The typical Modulation Transfer Function graph shown in FIG. 8 depicts the resolving power of an optical system consisting of a series of lenses, e.g., the human eye with a corrective lens, with that theoretically achievable.

The object bars below the X-axis show, from zero to the cutoff frequency, bars with increasing spatial frequency. The zero to one scale on the Y-axis is the measure of resolution of the bars by an optical system and that theoretically achievable at the diffraction limit. At a Y value of one, the bars are sharply distinguished into black and white images. As the Y value decreases, there is increasing "graying" of white into black of the images. Ultimately at a Y value of zero the bars cannot be distinguished at all.

The modulation can be determined by calculating the graying of the black and white bars at each spatial frequency into a maximum and minimum level. The MTF modulation is the (max−min)/(max−min) contrast. The MTF will be limited in value to a certain level called the "diffraction limit", which would be that level of modulation contrast achievable by a perfect optical system.

The resolving power of an optical instrument of any type is defined as a measure of the sharpness with which small images very close together can be distinquished and is directly proportional to the diameter of the objective aperture and inversely proportional to the wavelength of the light. The interference pattern resulting from rays passing through different parts of an opening or coming from different points around an opaque object and then unite at a point is the manifestation of diffraction. Diffraction and interference effects are characteristic of all wave phenomena. Diffraction thus limits the resolving power of all optical instruments.

When bars of black and white are coarse and widely spaced, a lens has no difficulty in accurately reproducing them. But as the bars get closer together diffraction and aberrations in the lens cause some light to stray from the bright bars into the dark spaces between them, with the result that the light bars get dimmer and the dark spaces get brighter until eventually there is nothing to distinguish light from darkness and resolution is lost.

MTF is calculated by tracing a large number of rays through the system, and evaluating the distribution density of these rays in the image position. The rays at this image position are located in the image "spot". The smaller the spot size, the better the image. The method by which the spot diagram is transformed to the MTF is as follows: the image of a point object is called a point spread function, since some blurring has occured in passing through the system. The image has thus spread. By applying a Fourier Transform function to the point or spot spread function, a graph of the MTF is generated. The MTF frequency goes from zero ("DC" in electrical engineering terms) to the maximum, or cutoff frequency, beyond which the object cannot be resolved in the image.

Optical systems can be optimized by varying the thickness, curvature, surface asphericity, material etc. of one or several surfaces Known numerical methods using computers allow rapid evaluation of the result of varying these parameters, in terms or aberration, spot size or MTF.

This design method requires an analysis of the density of the rays in the image position. This analysis is done by using a Fourier Transform function to generate modulation transfer frequencies A computer is used to allow the necessarily vast number of calculations to be performed in a reasonable time period An example of the results of such calculations is presented in FIGS. 9A through 9F. These Figures compare the modulation transfer frequency to the diffraction limit in a myopic eye-lens system, with each figure showing he results for a different lens curvature. These results indicate that the best lenses are those having a hyperbolic surface where $\kappa$ is between $-1$ and $-2$.

For the human eye/corrective lens model, one is constrained to changes in the corrective lens.

When used as a contact lens, the present invention preferably comprises a convex aspheric front surface and a concave spherical back surface that conforms to the curvature of the eye for a comfortable fit.

When in the form of an intraocular lens, the lens preferably will have one convex aspheric surface. The opposite surface preferably will be planar, concave spherical, convex aspheric, concave aspherical, or convex spherical. However, other embodiments are possible.

When used in spectacles the lens may comprise front and back surfaces which are independently concave or convex, and either one or both of these surfaces may be aspheric. Typically, the front surface will be convex and the back surface will be concave.

Another approach used to correct visual focal problems is surgical intervention, where the eye is mechanically cut or reshaped by a laser. In particular, excimer laser sculpting methodology is suitable in practicing the present invention. In this case, the appropriate hyperbolic corneal shape for optimal vision would be determined using the method of the present invention, and the shape then produced by this known technique. The result would require no additional corrective lens (even for most astigmats or presbyopes) and produce visual acuity better than a naturally "perfect" spherical lens.

Although the advantages of the present invention may be obtained in a system having a single aspheric surface, the present invention also includes the use of multiple aspheric surfaces, either in a single lens or in a combination of lenses.

A lens according to the present invention may be formed from any suitable high quality optical material, such as optical glass or plastic, but preferably the lens is made of optical quality transparent molded plastic. Suitable materials also include polymers (including fluoropolymers), resinous materials, solid or semi-solid gelatinous materials, rigid gas permeable materials, and the like. A contact lens constructed according to the present invention is preferably made of a hydrophilic polymer polmerized from a methacrylate based monomer. A lens according to the present invention may be incorporated into spectacles, but the preferred embodiments are contact lenses and intraocular lenses.

Many embodiments and variations of this invention will occur to those skilled in the art. The present invention is not limited to the embodiments described and illustrated, but includes every embodiment consistent with the foregoing description and the attached drawings that falls within the scope of the appended claims.

What is claimed is:

1. A method of constructing a lens for focusing light on the retina of the eye comprising the steps of:
   a) constructing a Fourier Transform function model that generates modulation transfer frequencies for the human eye and a preliminary lens, said lens having at least one rotationally symmetric surface defined by the equation:

$$X = \frac{Y^2}{r + [r^2 - (\kappa + 1)Y^2]^{\frac{1}{2}}}$$

where X is the aspheric surface point at position Y, r is the central radius, and $\kappa$ is commonly used aspheric constant, wherein the value of $\kappa$ is less than or equal to $-1$,
   b) performing an analysis using the model so constructed to trace light ray paths through the lens-eye system,
   c) varying the value of the aspheric constant, $\kappa$, for the preliminary lens to achieve a lens-eye system with a trace of light ray paths optimized for sharpest focus by minimizing retinal spot size of said rays.

2. The method of claim 1 wherein the lens so constructed is a contact lens.

3. The method of claim 1 wherein the value of $\kappa$ is varied between about $-1$ and about 31 2 in optimizing the performance of the corrective lens-eye system.

4. The method of claim 1 wherein the modulation transfer frequency is compared to the diffraction limit to optimize the corrective lens-eye system.

5. The method of claim 1 wherein the eye in the corrective lens-eye system is emmetropic and the optimization process produces vision that exceeds that of the normal eye.

6. The method of claim 1 wherein the corrective lens-eye system is optimized by positioning the focused image closest to the retina.

* * * * *

UNITED STATES PATENT AND TRADEMARK OFFICE
CERTIFICATE OF CORRECTION

PATENT NO. : 5,050,981
DATED : September 24, 1991
INVENTOR(S) : Jeffrey H. Roffman It is certified that error appears in the above-identified patent and that said Letters Patent is hereby corrected as shown below:

In claim 3, column 8, line 54, delete "about 31 2" and insert -- about -2 --

Signed and Sealed this

Twenty-sixth Day of January, 1993

Attest:

STEPHEN G. KUNIN

*Attesting Officer*  *Acting Commissioner of Patents and Trademarks*